United States Patent

Zelazoski et al.

Patent Number: 5,536,555
Date of Patent: Jul. 16, 1996

[54] LIQUID PERMEABLE, QUILTED FILM LAMINATES

[75] Inventors: Gregory A. Zelazoski, Woodstock; William A. Georger, Canton; Cheryl A. Perkins, Roswell, all of Ga.

[73] Assignee: Kimberly-Clark Corporation, Neenah, Wis.

[21] Appl. No.: 382,951

[22] Filed: Feb. 1, 1995

Related U.S. Application Data

[63] Continuation of Ser. No. 169,479, Dec. 17, 1993, abandoned.

[51] Int. Cl.⁶ ........................................ B32B 3/10
[52] U.S. Cl. .................... 428/138; 128/849; 156/73.1; 156/84; 156/85; 156/163; 156/164; 156/229; 156/257; 156/308.4; 428/131; 428/136; 428/137; 428/152; 428/198; 428/283; 428/284; 428/296; 428/297; 428/298; 428/373; 604/358; 604/378
[58] Field of Search .................... 428/131, 136, 428/137, 138, 198, 152, 283, 284, 296, 297, 298, 373; 128/849; 156/73.1, 84, 85, 163, 164, 229, 257, 308.4; 604/358, 378

[56] References Cited

U.S. PATENT DOCUMENTS

| | | | |
|---|---|---|---|
| 2,834,809 | 5/1958 | Schutte et al. | 92/3 |
| 2,867,560 | 1/1959 | Strawinski | 154/124 |
| 2,877,765 | 3/1959 | Bunyan | 128/156 |
| 2,896,618 | 7/1959 | Schaefer | 128/156 |
| 2,908,064 | 10/1959 | Lauterbach et al. | 28/72 |
| 2,923,298 | 2/1960 | Dockstader et al. | 128/296 |
| 3,236,238 | 2/1966 | Morse | 128/290 |
| 3,276,944 | 10/1966 | Levy | 161/150 |

(List continued on next page.)

FOREIGN PATENT DOCUMENTS

| | | |
|---|---|---|
| 803714 | 1/1969 | Canada . |
| 0301599 | 2/1989 | European Pat. Off. . |
| 0321980 | 6/1989 | European Pat. Off. . |
| 0360929 | 4/1990 | European Pat. Off. . |
| 0589225 | 3/1994 | European Pat. Off. . |
| 684327 | 8/1994 | Switzerland . |
| 2259018 | 3/1993 | United Kingdom . |
| WO92/14429 | 9/1972 | WIPO . |
| WO88/05269 | 7/1988 | WIPO . |
| WO92/11830 | 9/1990 | WIPO . |
| WO93/11726 | 7/1992 | WIPO . |
| WO93/11725 | 6/1993 | WIPO . |
| WO94/00292 | 1/1994 | WIPO . |

OTHER PUBLICATIONS

Search Report, Application No. GB 9425381.0, 20 Feb. 1995.
Search Report, Application No. FR 9415124, 19 May 1995.
Search Report, Application No. PCT/US 94/14403, 19 May 1995.
NRL Report 4364, "Manufacture of Super–Fine Organic Fibers" by V. A. Wendt, E. L. Boone and C. D. Fluharty.
NRL Report 5265, "An Improved Device For The Formation of Super–Fine Thermoplastic Fibers" by K. D. Lawrence, R. T. Lukas and J. A. Young.

*Primary Examiner*—James J. Bell

[57] ABSTRACT

Disclosed herein is a quilted film laminate wherein a film having a plurality of generally parallel slits is laminated to a substrate layer such as a fibrous nonwoven web. Due to processing conditions, once the slit film layer and substrate layer have been laminated to one another, the composite is allowed to retract thereby giving the composite a puckered or quilted appearance with an undulating surface. The undulating surface also causes the slits to form a plurality of openings which are generally perpendicular to the central plane of the film. In addition, due to the undulating nature of the surface of the film, the apertures so created reside in, above and below the central plane of the film layer. The composite so produced has a wide variety of uses not the least of which include a cover material or body side liner for personal care absorbent products. The process for producing the composite is also disclosed.

21 Claims, 5 Drawing Sheets

U.S. PATENT DOCUMENTS

| | | | |
|---|---|---|---|
| 3,307,545 | 3/1967 | Surowitz | 128/156 |
| 3,338,992 | 8/1967 | Kinney | 264/24 |
| 3,341,394 | 9/1967 | Kinney | 161/72 |
| 3,423,266 | 1/1969 | Davies et al. | 156/167 |
| 3,466,212 | 9/1969 | Clayton et al. | 156/199 |
| 3,502,538 | 3/1970 | Petersen | 161/150 |
| 3,502,763 | 3/1970 | Hartmann | 264/210 |
| 3,542,615 | 11/1970 | Dobo et al. | 156/181 |
| 3,543,750 | 12/1970 | Meizanis | 128/156 |
| 3,687,797 | 8/1972 | Wideman | 161/129 |
| 3,692,618 | 9/1972 | Dorschner et al. | 161/72 |
| 3,802,817 | 4/1974 | Matsuki et al. | 425/66 |
| 3,814,101 | 6/1974 | Kozak | 128/287 |
| 3,849,241 | 11/1974 | Butin et al. | 161/169 |
| 3,886,941 | 6/1975 | Duane et al. | 128/287 |
| 3,929,135 | 12/1975 | Thompson | 128/287 |
| 3,949,127 | 4/1976 | Ostermeier et al. | 428/137 |
| 3,965,906 | 6/1976 | Karami | 128/287 |
| 3,967,623 | 7/1976 | Butterworth et al. | 128/287 |
| 4,041,951 | 8/1977 | Sanford | 128/287 |
| 4,321,924 | 3/1982 | Ahr | 128/287 |
| 4,327,730 | 5/1982 | Sorensen | 128/287 |
| 4,340,563 | 7/1982 | Appel et al. | 264/518 |
| 4,446,189 | 5/1984 | Romanek | 428/152 |
| 4,469,735 | 9/1984 | Torkhan | 428/154 |
| 4,525,407 | 6/1985 | Ness | 428/138 |
| 4,573,989 | 3/1986 | Karami et al. | 604/381 |
| 4,606,964 | 8/1986 | Wideman | 428/152 |
| 4,626,254 | 12/1986 | Widlund et al. | 604/383 |
| 4,652,487 | 3/1987 | Morman | 428/138 |
| 4,657,802 | 4/1987 | Morman | 428/152 |
| 4,668,566 | 5/1987 | Braun | 428/286 |
| 4,690,679 | 9/1987 | Mattingly et al. | 604/383 |
| 4,692,368 | 9/1987 | Taylor et al. | 428/137 |
| 4,720,415 | 1/1988 | Vander Wielen et al. | 428/152 |
| 4,725,473 | 2/1988 | Van Gompel et al. | 428/156 |
| 4,761,324 | 8/1988 | Rautenberg et al. | 428/198 |
| 4,781,966 | 11/1988 | Taylor | 428/152 |
| 4,798,604 | 1/1989 | Carter | 604/383 |
| 4,801,494 | 1/1989 | Datta et al. | 428/283 |
| 4,834,738 | 5/1989 | Kielpikowski et al. | 604/385.2 |
| 4,842,596 | 6/1989 | Kielpikowski et al. | 604/385.2 |
| 4,847,134 | 7/1989 | Fahrenkrug et al. | 428/138 |
| 4,880,682 | 11/1989 | Hazelton et al. | 428/152 |
| 4,891,258 | 1/1990 | Fahrenkrug | 428/138 |
| 4,902,553 | 2/1990 | Hwang et al. | 428/156 |
| 4,908,026 | 3/1990 | Sukiennik et al. | 604/378 |
| 4,916,005 | 4/1990 | Lippert et al. | 428/192 |
| 4,935,287 | 6/1990 | Johnson et al. | 428/198 |
| 4,981,747 | 1/1991 | Morman | 428/198 |
| 5,057,361 | 10/1991 | Sayovitz et al. | 428/290 |
| 5,078,710 | 1/1992 | Suda et al. | 604/383 |
| 5,089,075 | 2/1992 | Sonoda | 156/244.18 |
| 5,114,781 | 5/1992 | Morman | 428/198 |
| 5,135,521 | 8/1992 | Luceri et al. | 604/383 |
| 5,143,679 | 9/1992 | Weber et al. | 264/288.8 |
| 5,151,314 | 9/1992 | Brown | 428/138 |
| 5,188,625 | 2/1993 | Van Iten et al. | 604/383 |
| 5,208,098 | 5/1993 | Stover | 428/284 |
| 5,244,716 | 9/1993 | Thornton et al. | 428/198 |
| 5,248,309 | 9/1993 | Serbiak et al. | 604/368 |
| 5,264,268 | 11/1993 | Luceri et al. | 428/138 |

LIQUID PERMEABLE, QUILTED FILM LAMINATES

This application is a continuation of application Ser. No. 08/169,479 entitled "Liquid Permeable, Quilted Film Laminates" and filed in the U.S. Patent and Trademark Office on Dec. 17, 1993 now abandoned.

FIELD OF THE INVENTION

The present invention is directed to a quilted film laminate. More particularly, the quilted film laminate of the present invention includes embodiments wherein the film is laminated to a fibrous nonwoven substrate thereby making it particularly suitable as a body side liner material for personal care products including diapers, sanitary napkins, training pants, incontinence garments, bandages and the like.

BACKGROUND OF THE INVENTION

Almost all personal care absorbent articles include a body side liner material or cover, an absorbent core and some type of backing material which is generally liquid impervious to help prevent leakage. The types of cover materials have basically fallen into two main groups with the division being based, at least in part, upon two schools of thought as to aesthetic preferences. In the area of feminine care and sanitary napkins, the market is polarized in two segments, women who prefer clean and dry film covers and women who prefer soft, cloth-like nonwoven covers. The Procter and Gamble Company of Cincinnati, Ohio markets sanitary napkins under the trademark ALWAYS® with an apertured film as the cover material. This product is allegedly made in accordance with the teachings of U.S. Pat. No. 3,929,135 to Thompson. Molnlycke AB, Goteborg, Sweden markets a sanitary napkin with a film layer laminated to a nonwoven. The film layer has openings with tabs designed for transporting fluids. This product is allegedly made in accordance with the teachings of Widlund, U.S. Pat. No. 4,626,254. The advantage of such film covers for sanitary napkins is that they provide a relatively clean and dry surface as menses tends to pass through the film layer and into the interior of the absorbent product. A drawback, however, it that such film layers do not provide the degree of softness and comfort that a nonwoven cover material can provide. Another drawback is the smooth, slick, non-cloth-like feel that many films possess. This is due, at least in part, to the two-dimensional nature of film covers. Conversely, nonwoven-based cover materials such as KOTEX® Fem Care pads from the assignee of record are very soft and cloth-like in feel but, given the viscosity of menses, tend to retain more of the menses at or just below the surface of the cover material which, in turn, makes the product suffer from the standpoint of properties such as cleanliness and dryness. In view of the foregoing deficiencies of both nonwoven and film covers, it would be desirable to form a material that combined the attributes of both types of covers in a more three-dimensional structure. Such a material would tend to reduce the polarity in acceptance of cover materials and products. As a result, there is a need for an improved material which, among other applications, can be used as a body side cover for personal care absorbent products.

SUMMARY OF THE INVENTION

The present invention is directed to a quilted film laminate or composite which provides a good blend of the positive properties from both film and fibrous nonwoven cover materials. Due to the nature of the perforation of the film layer, the selection of the substrate material to which the film is laminated and the method of by which the composite is assembled, there is provided a cover material which is very soft and cloth-like to the touch while still providing good fluid intake rates and protection against rewet when used as a cover material for personal care products. In addition, due to the nature of the materials used to form the composite, the composite can be used with either the film side or the nonwoven side positioned adjacent the wearer in personal care absorbent article applications. Beyond the area of personal care products, the material of the present invention has many other uses, not the least of which is a material which can be used in the construction of absorbency areas in surgical drapes, etc. Given the excellent absorption rates for menses which is a blood-based fluid, the material of the present invention would be well-suited for use about the incise areas of surgical drapes to contain and retain fluids.

The quilted film laminate of the present invention includes a film layer and a substrate layer joined to one another at a plurality of spaced-apart bond points which can be created by using heat and pressure or adhesives. The film contains a plurality of small generally parallel slits. Once the two layers have been bonded together, the composite is caused to retract by one of several different processes thereby creating a plurality of gathers or puckers in the film layer which reside in, above and below the general plane of the film layer. Depending upon the degree of retraction and thus the degree of gathering or puckering of the composite, the slits defined in the film layer will tend to open thereby creating a plurality of openings or apertures which extend vertically rather than horizontally with respect to the plane of the film, and which also will reside in, above and below the general plane of the film layer.

Personal care absorbent articles will typically comprise a body side liner and a back side liner with an absorbent core disposed therebetween. The quilted film laminate of the present invention can be used as the body side liner for such personal care absorbent articles as it provides good intake of liquids and resistance to rewet. Examples of such personal care products include, but are not limited to, feminine napkins, diapers, training pants, incontinence garments, bandages and the like. In such applications, it is oftentimes desirable to mask the absorbed fluid so as to provide a more aesthetically appealing product once it has been soiled. For this purpose, the film layer can contain an opacifying agent such as titanium dioxide in a weight percent of from about 4 to about 12 percent based upon the total weight of the film.

The process for forming the quilted film laminate involves placing a film layer defining a plurality of generally parallel slits in generally face-to-face relationship with a substrate layer and then bonding the film layer to the substrate layer to form a composite. To form the puckers in the film layer, at least one of the film and/or substrate layers is caused to retract thereby forming the puckers and also creating a plurality of openings formed by the slits which reside in, above and below a central plane defined by the film layer. The puckers in the film layer can be imparted several different ways. One method is by stretching the substrate layer prior to the bonding of the substrate layer to the film layer. After the two layers are bonded to one another, the stretching forces are relaxed and the substrate layer retracts thereby forming the puckers and the openings in the slits. A second way of forming puckers is to form one of the two layers from a heat shrinkable material. Once the two layers have been bonded to one another, heat can be applied to the composite thereby activating the heat shrinkable layer and causing it to retract which in turn causes the puckers and openings to form. In addition, either one or both of the two layers can be stretched and the stretching can be in the same or different directions to create the puckers in the composite. Lastly, a heat shrinkable material can be used with a stretched material thereby combining the processes for forming the puckers and openings.

DETAILED DESCRIPTION OF THE INVENTION

The present invention is directed to a quilted film laminate. The laminate is designed to be liquid permeable thereby making it suitable for a wide variety of uses including, but not limited to, a liner material for personal care products including feminine pads or sanitary napkins, diapers, training pants, incontinence garments, bandages and the like. In addition, the laminate could be used in the construction of meat and poultry pads, wipers and absorbents in general. Other applications would include fluid management materials for health care applications such as absorbents for use around the incise portion of surgical drapes. If made oleophilic, the laminate of the present invention could also be used in the construction of oil absorption materials. The foregoing list of uses should be considered as illustrative only as other uses are also contemplated to be within the scope of the present invention.

Figure 1:
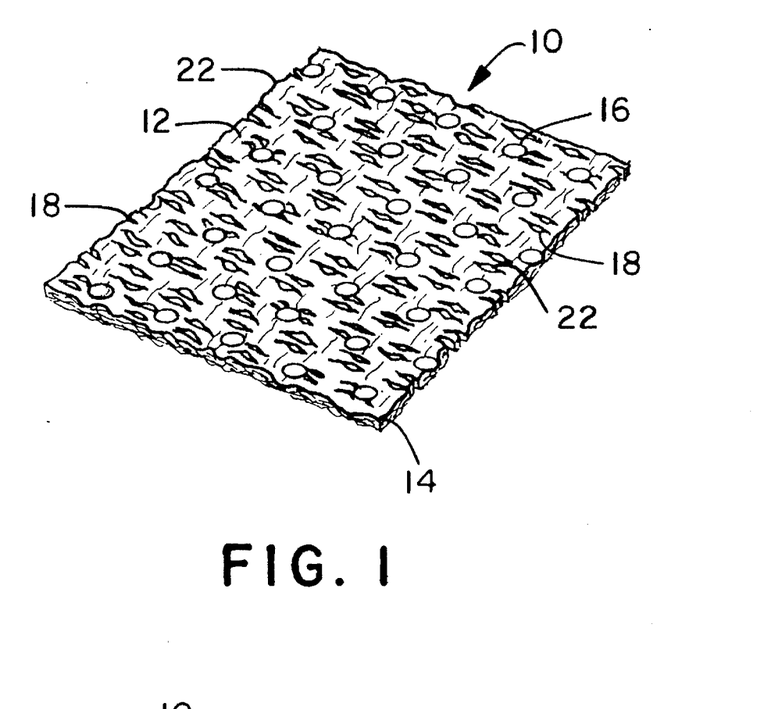
FIG. 1 is a perspective view of a liquid permeable, quilted film laminate according to the present invention.
Figure 2:
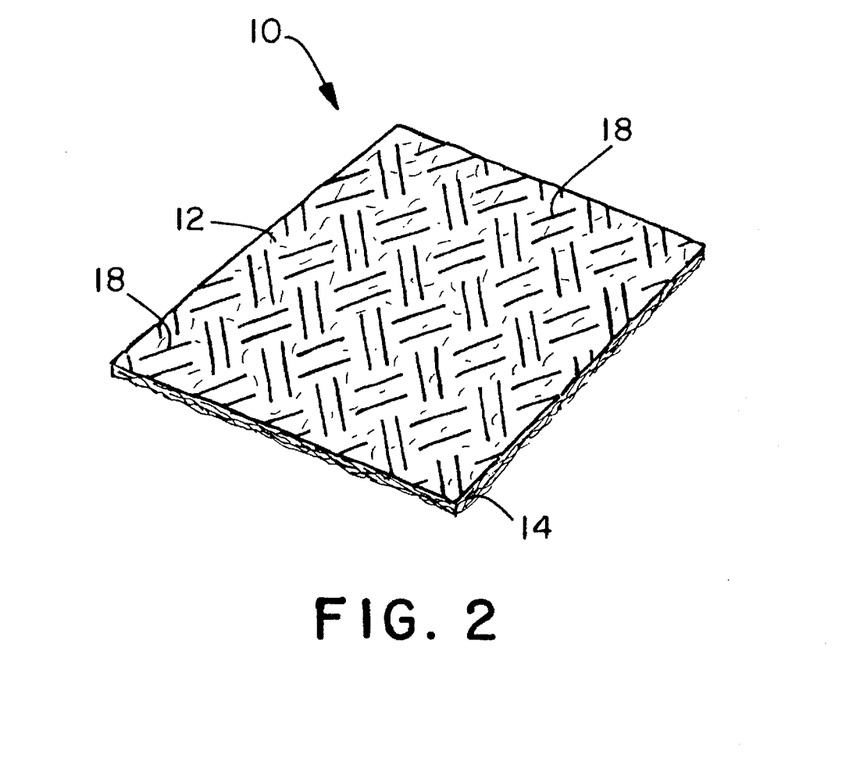
FIG. 2 is a perspective view of a liquid permeable, quilted film laminate according to the present invention.
Figure 3:
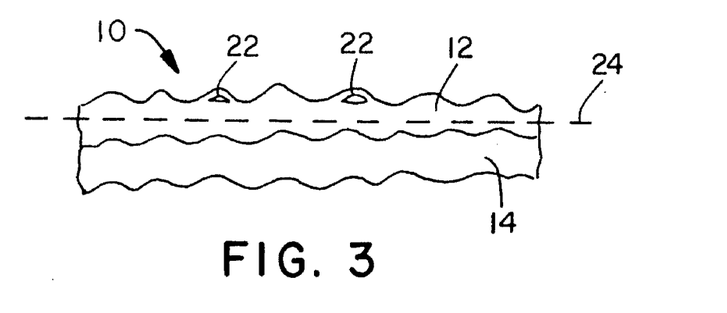
FIG. 3 is a cross-sectional side view of a liquid permeable, quilted film laminate according to the present invention.
Figure 4:
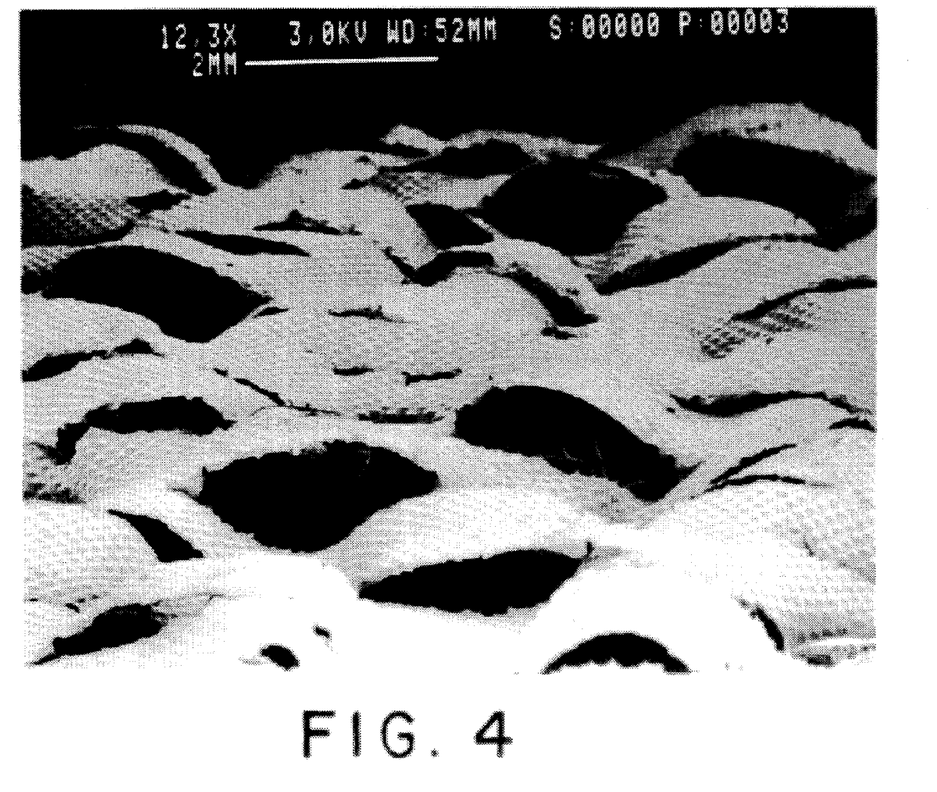
FIG. 4 is a photomicrograph of a liquid permeable, quilted film laminate according to the present invention.

Referring to FIGS. 1 through 3, the quilted film laminate 10 of the present invention includes a film layer 12 and a substrate layer 14 joined to one another at a plurality of spaced-apart bond points 16. As can be seen in FIGS. 1 and 2, the film layer 12 contains a plurality of slits 18, the nature of which, will be described in further detail below. After bonding has been completed, the laminate or composite 10 is caused to retract thereby forming a plurality of gathers or puckers. "Puckers" or "gathers" are undulations in a material or composite which extend above and below the general plane of the film layer. Depending upon the degree of retraction and thus the degree of gathering or puckering of the composite 10, the slits 18 defined in film layer 12 will tend to open thereby creating a plurality of openings 22 which can also been seen in the photomicrograph of FIG. 4. An imaginary center plane 24 can be defined generally equidistant between the upper and lower surfaces of the puckered film layer 12. With this plane acting as a reference point, the openings 22 reside in, above and below this central plane 24 thus creating openings at a multitude of vertical heights within the thickness of the overall composite 10. As will be shown by the examples and data below, the resultant material when used as a body side liner material or cover for personal care products provides good intake of liquids and resistance to rewet.

The film layer 12 can be made from a number of polymers including homopolymers, copolymers and blends of polyolefins, acetate polymers, polyesters and the like. The particular polymer selection can be influenced by the desire for particular attributes including strength, softness and opacity. For personal care product applications, film thicknesses will typically range between about 0.4 and about 2.0 mils with 0.75 to 1 mils being more desirable. It should be noted, however, that larger or smaller film thicknesses are also contemplated to be within the scope of the present invention depending upon the end use.

Certain end use applications such as sanitary napkins require that the body side liner or cover material be able to mask body exudates to impart a cleaner and dryer appearance. To increase masking or opacity, additives such as pigments, fillers and other materials, collectively referred to as opacifying agents, may be added to the film. Examples of opacifying agents would include titanium dioxide (Whiterutile grade), titanium dioxide complexes (yellow, buff, green, and blue) iron oxides (red, yellow, tan and black) ultramarine blue and green, cobalt complexes (blue and turquoise), iron blue and chrome green, lead chromates and molybdates (yellow and orange) cadmiums (yellow, orange and red), calcium carbonate, carbon black, phthalocyanines (blue and green) and quinacridones (red and magenta). For sanitary napkin applications it has been found that adding between about 4 and about 12 percent by weight of an opacifying agent such as titanium dioxide to the film, based upon the total weight of the film, will enhance the masking ability of the film. It should be noted, however, that larger or smaller quantities of opacifying agents can be added depending upon the particular end use.

Many polymers used to make the film layer 12 are naturally hydrophobic which may make them suitable for certain end use applications. In other applications, such as personal care products, if the quilted film laminate of the present invention is to be employed as a cover material, it is more desirable that the film layer 12 be hydrophilic. As a result, internal and/or topical wetting agents can be added to the film layer 12 to make the film layer hydrophilic. Such wetting agents and their use with films are well known to those of ordinary skill in the art.

It may be desirable to impart other properties or characteristics to the film layer 12. As a result, other additives can be incorporated into the film layer 12 to impart such properties or characteristics. For example, it is possible to create films which are breathable, thereby permitting the film layer 12 to pass water vapor from one surface through to the other, even between the openings.

To permit fluid transport through the composite 12, the film layer 12 is provided with a plurality of slits 18. The slits 18 are distinguishable from apertures in that when making the slits 18 in the film 12, little or no material is removed when cutting through the film layer. As a result, a slit film, unlike an apertured film, provides limited visibility through the slits when the film is flat. As shown in FIG. 1, the slits 18 are provided in pairs which are generally parallel to one another. By "generally parallel" it is meant that the intersection of the axes of the slits forms an interior angle which is less than or equal to 45°. Referring to FIG. 1, the pairs of slits 18 are provided in staggered rows with the axes of all these slits and pairs of slits being generally parallel to one another due to their alignment in the same general direction.

In FIG. 2 the pairs of slits 18 are provided in a herringbone design.

Figure 5:
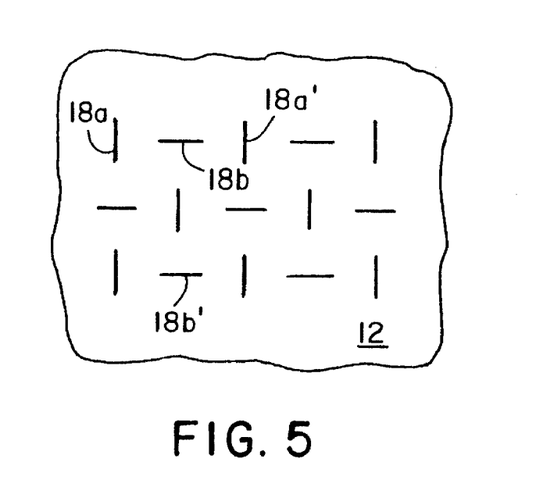
FIGS. 5 through 9 are examples of slit patterns which can be used for the film layer of the liquid permeable, quilted film laminate according to the present invention.

Other slit patterns are also contemplated to be within the scope of the present invention. Several such patterns are shown in FIGS. 5 through 9. In FIG. 5 there is shown a plurality of slits 18 which have an alternating perpendicular pattern. In such a configuration there are a plurality of pairs of slits 18a, 18b and 18a', 18b' which are generally parallel to one another yet separated by intervening slits.

Figure 6:
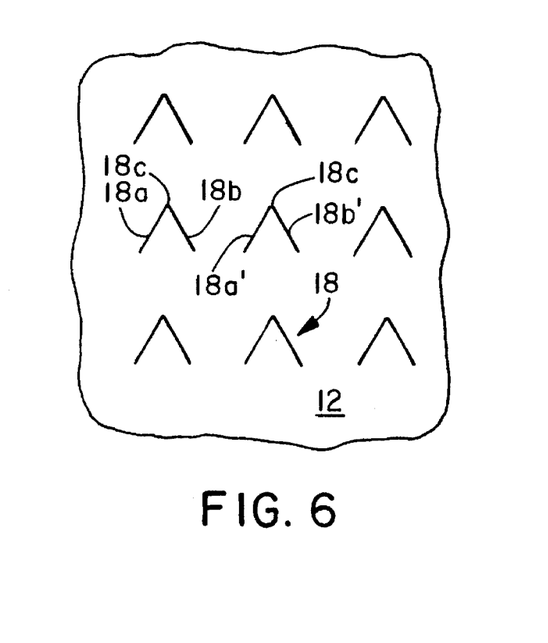

FIG. 6 depicts a plurality of V-shaped slits 18a, 18b and 18a', 18b' which each respectively intersect at points 18c and 18c'. In this configuration, it can be seen that slits 18a and 18a' are generally parallel to one another as are 18b and 18b'.

Figure 7:
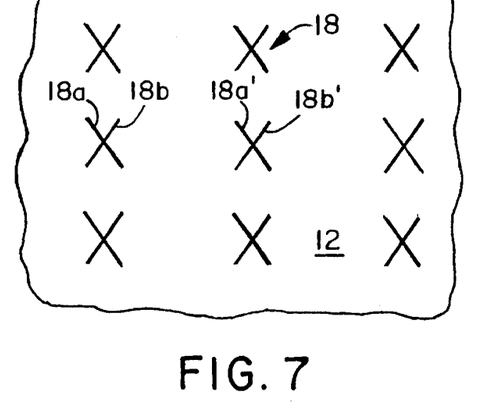

In FIG. 7, the slits 18 form a series of X's or cross hatches. See for example, slits 18a, 18b and 18a', 18b'. Again with this configuration it can been seen that there are pairs of generally parallel slits including pairs 18a, 18a' and 18b, 18b.

Figure 8:
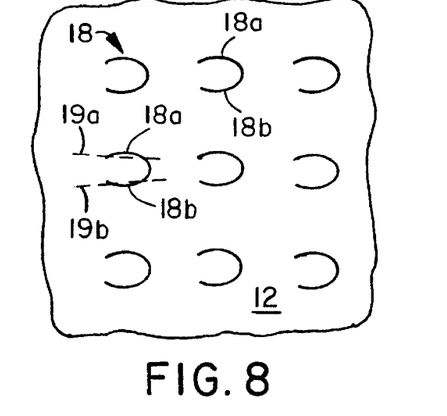
Figure 9:
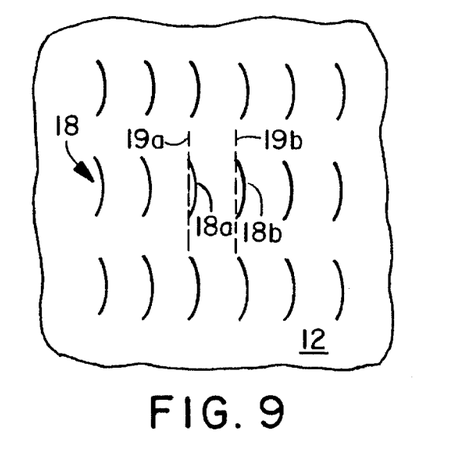

In FIGS. 8 and 9 there are shown, respectively, horseshoe-shaped slits and crescent-shaped slits. The horseshoe-shaped slits in FIG. 8 can be viewed as having two curved sides 18a and 18b which are joined to one another. Normalized axes 19a and 19b can be drawn through the respective legs 18a and 18b of the horseshoe-shaped slits and an extension of these two axes would indicate that the two sides 18a and 18b are generally parallel to one another given the present definition. The same type of normalized axes 19a and 19b can be drawn through the crescent-shaped slits 18a and 18b in FIG. 9 and an extension of these axes again indicates that the pairs of slits 18a and 18b are generally parallel to one another.

The advantage of slits versus apertures to meet end use applications resides in the ability to vary the degree of opening of the film layer 12 through stretching and retraction. The degree of openness of the film layer 12 and thus the composite 10 will depend upon the number of slits and the length of the slits as well as the degree of stretching of the film and the amount of puckering or gathering of the overall composite 10. The slit density can be defined as the average total slit length per unit area and can be measured in such units as total inches per square inch. While the slit density can be varied for a particular end-use application, it has been found that for personal care absorbent articles and sanitary napkins in particular, the slit density should be at least five total inches per square inch (4 cm/cm$^2$). Below this number, there are insufficient openings created when the composite is gathered to allow for effective transport of body exudates such as menses and urine through the composite 10. Care should be taken however to balance the number of slits with the strength of the film as excessive slitting can result in a composite which tears under very little stress.

Bonded to the slit film layer 12 is a substrate layer 14 which can provide extra strength, bulk and caliper to the overall composite 10. From the standpoint of economics, one of the less costly materials for the substrate 14 is a fibrous nonwoven web. It is believed to be possible, however, to use other materials for the substrate layer 14 including films, foams, knitted materials, woven materials, scrim and netting. Bonding of the film layer 12 to the substrate layer 14 may be accomplished in any number of ways including, but not limited to, pressure, heat and pressure, ultrasonic bonding, adhesives, stitching, needling and the bonding of elastic threads with or without adhesives between the two layers as well as combinations of the foregoing. Three of the most efficient ways of bonding the layers together are ultrasonic bonding, adhesives (hot-melt, water-based and solvent-based) and thermomechanical bonding such as through the use of heated and patterned bonding rolls. Whatever bonding process is chosen, the resultant nonwoven should have sufficient integrity such that it can be expanded from a first or original length to a second and extended length and then, after bonding, retract to a third length which is less than the second or stretched length.

In personal care product applications, when constructing a cover material, nonwoven substrates seem to work particularly well. With slit film/nonwoven laminates, it is possible to use the composite as a body side liner with either surface facing the wearer. Due to the difference in fluid properties of various body exudates, it is been found that film side up configurations work well for menses while nonwoven side up configurations work well for diapers though either configuration can be used for either type of body exudate and end use product. There appears to be no apparent restriction as to the type of fibrous nonwoven webs which can be used to make the substrate layer 14. The nonwoven webs may be bonded carded webs, spunbond webs, meltblown webs, air laid webs, wet laid webs and solution spun webs all of which may include composites or blends of several types of fibers including natural and synthetic. In addition, other additives may be incorporated into the nonwoven webs such as, for example, hydrocolloids or superabsorbents in particulate and/or fiber form.

Meltblown and spunbond fibrous nonwoven webs work particularly well as materials from which to form the substrate layer 14. Meltblown webs are made from fibers formed by extruding a molten thermoplastic material through a plurality of fine, usually circular dye capillaries as molten threads or filaments into a high-velocity heated air stream which attenuates the filaments of molten thermoplastic material to reduce their diameters. Thereafter, the meltblown fibers are carried by the high-velocity gas stream and are deposited on a collecting surface to form a web of randomly dispersed meltblown fibers. The meltblown process is well known and is described in various patents and publications, including NRL Report 4364, "Manufacture of Super-Fine Organic Fibers" by V. A. Wendt, E. L. Boone and C. D. Fluharty; NRL Report 5265, "An Improved Device For the Formation of Super-Fine Thermoplastic Fibers" by K. D. Lawrence, R. T. Lukas and J. A. Young; and U.S. Pat. No. 3,849,241, issued Nov. 19, 1974 to Buntin et al.

Spunbond nonwoven webs are made from fibers which are formed by extruding a molten thermoplastic material as filaments from a plurality of fine, usually circular, capillaries in a spinneret with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563, Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent Number 803,714.

A particularly well-suited spunbonded nonwoven web for the substrate layer 14 is made from side-by-side polyethylene/polypropylene spunbond bicomponent fibers. The process for forming such fibers and resultant webs includes using a pair of extruders for separately supplying both the polyethylene and the polypropylene to a bicomponent spinneret. Spinnerets for producing bicomponent fibers are well known in the art and thus are not described in detail herein. In general, the spinneret includes a housing containing a spin pack which includes a plurality of plates having a pattern of openings arranged to create flow paths for directing the high melting and low melting polymers to each fiber-forming opening in the spinneret. The spinneret has openings arranged in one or more rows and the openings form a downwardly extending curtain of fibers when the polymers are extruded through the spinneret. As the curtain of fibers exit the spinneret, they are contacted by a quenching gas which at least partially quenches the fibers and develops a latent helical crimp in the extending fibers. Oftentimes the quenching air will be directed substantially perpendicular to the length of the fibers at a velocity of from about 100 to about 400 feet per minute at a temperature between about 45 and about 90°F.

A fiber draw unit or aspirator is positioned below the quenching gas to receive the quenched fibers. Fiber draw units or aspirators for use in meltspinning polymers are well known in the art. Exemplary fiber draw units suitable for use in the process include linear fiber aspirators of the type shown in U.S. Pat. No. 3,802,817 to Matsuki et al. and eductive guns of the type shown in the U.S. Pat. No. 3,692,618 to Dorshner et al. and U.S. Pat. No. 3,423,266 to Davies et al. The fiber draw unit in general has an elongated passage through which the fibers are drawn by aspirating gas. The aspirating gas may be any gas, such as air, that does not adversely interact with the polymers of the fibers. The aspirating gas can be heated as the aspirating gas draws the quenched fibers and heats the fibers to a temperature that is required to activate the latent crimps therein. The temperature required to activate the latent crimping within the fibers will range from about 110° F. to a maximum of less than the melting point of the low melting component polymer which, in this case, is the polyethylene. Generally, a higher air temperature produces a higher number of crimps.

The drawn and crimped fibers are deposited onto a continuous forming surface in a random manner, generally assisted by a vacuum device placed underneath the forming surface. The purpose of the vacuum is to eliminate the undesirable scattering of the fibers and to guide the fibers onto the forming surface to form a uniform unbonded web of bicomponent fibers. If desired, the resultant web can be lightly compressed by a compression roller before the web is subjected to a bonding process.

To bond the bicomponent spunbonded web a through-air bonder is used. Such through-air bonders are well known in the art and therefore need not be described in detail. In the through-air bonder, a flow of heated air is applied through the web to heat the web to a temperature above the melting point of the lower melting point component of the bicomponent fibers but below the melting point of the higher melting point component. Upon heating, the lower melting polymer portion of the web fibers are melted and the melted portions of the fibers adhere to adjacent fibers at the crossover points while the high melting polymer portions of the fibers tend to maintain the physical and dimensional integrity of the web.

The types of fibers which can be used to make the fibrous nonwoven webs can include staple length fibers as well as meltblown and spunbond fibers which are longer in length relative to staple fibers. The fibers themselves may be single polymer fibers or multiconstituent or component fibers such as bicomponent fibers including side-by-side, sheath/core and islands-in-the-sea type cross-sections. The fibers may be hollow fibers as well as straight or crimped. In addition, the fibers may have circular or irregular cross-sections such as bilobal, trilobal, etc. The fibers may be made from natural or synthetic materials. Examples of natural-based fiber materials include cellulose, cotton, rayon and wood pulp. Examples of synthetic fiber materials include polyolefins, polyesters, polyamides and polyvinyl alcohol and include homopolymers, copolymers and blends.

Fiber sizes for the fibers making up the fibrous nonwoven webs can be relatively uniform or can be a mixture of various sizes of fibers. For personal care product applications, fiber diameters in the range of about 5 to about 150 microns can be used. It is possible, however, to utilize fiber sizes ranging from submicron to several hundred microns depending upon the particular end use application.

The nature of the end use will also bear upon the basis weight of the nonwoven, however, here again the basis weight must be sufficiently great to allow expansion and retraction of the nonwoven substrate layer if gathering or puckering is not being caused solely by the use of a heat-shrinkable material. Generally, basis weights between about 0.3 and 2.2 ounces per square yard (osy) (about 14 and about 75 grams per square meter (gsm)) will work for personal care product applications.

An important feature of the present invention is the gathers or puckers 20 caused by expanding one of the layers, bonding the layers together and then retracting the overall composite. Prior to the bonding of the two layers together, one of the layers is stretched or expanded so that once the two layers are joined, the laminate and especially the film layer puckers. The gathers or puckers 20 increase the overall surface area per unit area thereby making the composite thicker and more bulky and causing a plurality of the slits to open up in the vertical direction thereby creating more effective passages for the transport of fluids through the thickness of the composite 10 from one surface to the other. These gathers or puckers can be created in several different ways.

The first method involves stretching one of the two layers in one direction prior to the bonding of the stretched layer to the non-stretched layer. Once the two layers have been bonded to one another the stretching or tensional forces can be relaxed thereby causing the composite to retract and gather or pucker. Thus, for example, the substrate layer can be stretched in the machine direction and then bonded to the film layer. Conversely, the film layer could be stretched and then bonded to the unstretched substrate layer. In addition, the substrate layer could be stretched in one direction as, for example, the machine direction (MD) while the film layer is stretched in another or second direction such as, for example, the cross direction (CD). With both the layers in their stretched forms, the two layers can then be bonded to one another and then allowed to retract thereby causing gathering or puckering in at least two directions.

A second method of imparting gathers or puckers to the quilted composite 10 involves making one of the two layers from a heat retractable or heat shrinkable material. Examples of such materials include oriented films that are not heat set and elastomeric materials made from resins including polyurethanes, polyesters, polyolefins and polyacetates. In this process, the heat shrinkable layer, whether film or nonwoven, is bonded to the other layer and, once bonded, the composite is subjected to a sufficient amount of heat to cause the heat shrinkable layer to retract thereby causing the composite to gather or pucker. Here again, either the film layer or the substrate layer can be made heat shrinkable. Care should be taken that the amount of heat needed to effect shrinking does not destroy the bonding between the layers.

A third method of imparting gathers or puckers to the composite 10 involves stretching one of the layers and bonding it to the other layer with the other layer being made from a heat shrinkable material. Once the two layers are bonded, the tension in the stretched layer can be relaxed and heat can be applied to the composite thereby providing two means within the same composite for creating gathers or puckers. If desired, the direction of orientation of the heat shrinkable material can be parallel with or skewed from the direction of stretching in the other layer to provide gathering or puckering in one or more directions.

A fourth way to impart gathers or puckers to the composite material 10 of the present invention would be to stitch the two layers together using elastic or heat shrinkable threads. Once the stitching was complete, the elastic threads would retract thereby gathering and puckering the composite material 10.

A fifth way to impart gathers or puckers to the material of the present invention would be to use elastic threads sandwiched between and bonded to the film layer 12 and substrate layer 14. The elastic threads would be stretched or elongated prior to their adhesion or bonding between and to the two layers. Once the bonding had been completed, the elastic threads would retract thereby gathering and puckering the composite material 10 of the present invention.

In much the same way as with the elastic threads, it is also possible to impart gathers or puckers to the composite material 10 of the present invention through the use of elastic or heat shrinkable scrim or netting materials sandwiched between and bonded to the film layer 10 and substrate layer 14 of the present invention.

The degree of gathering or puckering of the composite 10, is due at least in part, to the degree of retraction of the composite. In any one of the foregoing processes, the composite will have a first or original length which is greater than the second or extended length and a third or retracted length which will be less than the second length. Factors affecting the retraction will include the degree or percent to which a material can be heat shrunk and/or the extent to which a particular layer can be extended and whether or not all or a portion of the extension forces can be regained upon release of the tension in the stretched layer. In the personal care absorbent product area it has been found that when making body side liner material, it is advantageous to stretch a fibrous nonwoven substrate layer approximately 5 to 20 percent beyond its original or unstretched length prior to bonding to the film layer 12. Once the two layers have been bonded together, the tension on the fibrous nonwoven substrate layer 14 is released and the nonwoven layer retracts from its second or extended length to all or a portion of its original length. The degree of recovery or retraction is dependent upon the recovery properties of the substrate material as well as the degree of bonding of the composite, both of which can impede complete recovery.

The degree of bonding will affect the aesthetic properties of the composite 10 such as feel and smoothness. The degree of bonding will also affect the bulk of the composite 10 as well as the delamination characteristics of the composite 10. Generally, it has been found that small discrete bond points provide better bonding strength while maximizing the bulk and three-dimensional surface topography. However, it is also possible to use other bonding patterns such as lines, and other geometric or abstract designs as well as combinations of the foregoing. When using adhesives, care should be taken not to bond the film too heavily to the substrate layer as if this is the case, then it will be difficult for the slits to open up and form a plurality of openings.

Figure 10:
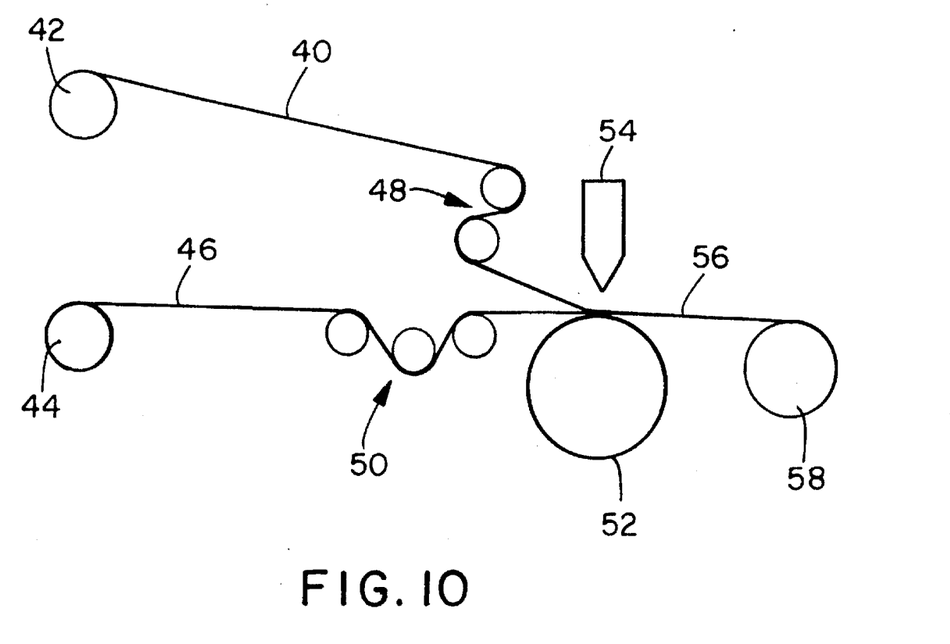
FIGS. 10 and 11 are schematic views of two processes for forming the liquid permeable, quilted film laminate of the present invention.
Figure 11:
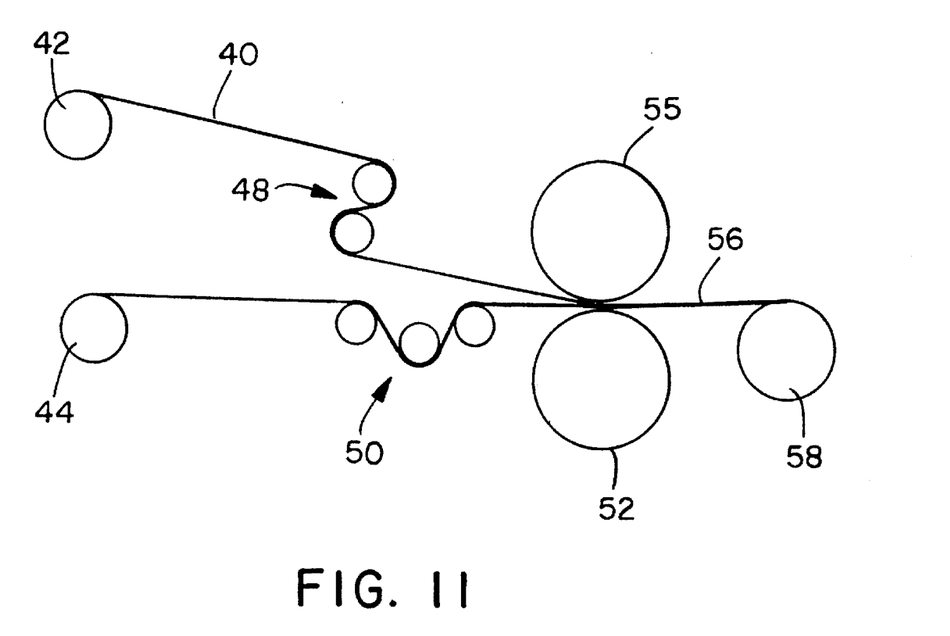

Two of the previously described processes for forming the quilted composite are shown in FIGS. 10 and 11. FIG. 10 depicts a process for forming a quilted film/fibrous nonwoven laminate using ultrasonic bonding techniques while FIG. 11 utilizes heat and pressure. Referring to FIG. 10, there is shown a supply of nonwoven material 40 being unwound from a supply roll 42. Unwound from a similar supply roll 44 is a supply of slit film 46 which has previously been slit. The nonwoven or substrate layer 40 passes through a pair of controlled S-wrapped rollers 48 driven or braked at a speed $V_1$ so that the substrate layer is stretched in the machine direction. At the same time, the film layer 46 is sent through a series of spreader rolls 50 whose function is to maintain uniform width with minimal wrinkles. The spreader rolls are traveling at a speed $V_2$ which is greater than $V_1$. The nonwoven layer 40 and the film layer 46 are brought into contact with one another between a pattern roll 52 and an ultrasonic horn 54 where the two layers are bonded to one another. At the point of bonding, the speed of the nonwoven layer and the speed of the film layer are the same, $V_2$. As a result, the nonwoven layer is bonded to the film layer while the nonwoven substrate in a stretched condition with the degree of stretch being a function of the speed differential between $V_1$ and $V_2$. After bonding takes place, the composite 56 is allowed to retract thereby gathering and puckering the composite prior to its accumulation on take up roll 58.

In FIG. 11, the same process and stretching techniques are used as described above with respect to the process shown in FIG. 10, the only difference being in the method of bonding the two layers 40 and 46 together. In FIG. 11, the ultrasonic horn 54 is replaced with a heated anvil roll 55 which together with the pattern bond roll 52 serve to bond the two layers 40 and 46 together.

Having described the materials and process for forming the quilted film laminate of the present invention, a series of examples were prepared to demonstrate the present invention. In addition, a series of tests were performed to determine the functional properties of the resultant materials. These examples, test procedures and results are presented below.

TEST METHODS

A series of tests were performed on the materials of the present invention including Frazier porosity, trapezoid tear, intake rate, rewet, run-off, thickness and surface smoothness.

Air permeability was measured using the Frazier porosity test. Air permeability is the rate of air flow through a material under a pressure differential between two fabric surfaces. Samples were tested on a Frazier Air Permeability Tester available from Frazier Precision Instrument Company of Gaithersburg, Md. The procedures used conformed to the specifications of Method 5450, Federal Test Methods Standard 191A except that the specimen size was 8 inches×8 inches (20.3×20.3 cm) rather than 7 inches×7 inches (17.8× 17.8 cm). The larger size made it possible to ensure that all sides of the specimen extended well beyond the retaining ring and facilitated clamping of the specimen securely and evenly across the orifice. In the procedure, air was drawn through the specimen and a calibrated orifice using a suction fan. By controlling the speed of the fan, the rate of air flow through the fabric was adjusted to obtain a pressure differential of 0.51 inches (13 mm) of water between the two surfaces. The amount of air flowing through the specimen was determined from the drop in pressure across a calibrated orifice as indicated by a vertical oil manometer. This reading was converted to an air flow rate using a conversion table provided by the manufacturer of the instrument. The results were expressed in cubic feet of air per square foot of specimen per minute or in cubic centimeters per square centimeter per second. The higher the number, the more permeable or porous the material.

To test the tear strength of the materials, a trapezoid tear test was conducted. This test was a measure of the tearing strength of a material or materials when a constantly increasing load was applied parallel to the length of the specimen. The test can be conducted on a constant rate of extension tester such as an Instron, model TM available from Instron Corporation of Canton, Mass. or a Thwing-Albert, Model INTELLECT II tester available from Thwing-Albert Instrument Company of Philadelphia, Pa.

The procedure was performed in accordance with the specifications of ASTM Standard Test Method D 1117-14 with the exception that the tearing load was calculated as the average of the first and highest peaks recorded rather than by use of the lowest and highest peaks. An outline of a trapezoid was drawn on a 3 inch×6 inch (7.6 cm×15.2 cm) specimen (the longer dimension in the direction being tested) and a small, preliminary cut was made on the shorter of the parallel sides. The specimen was clamped along the non-parallel sides of the trapezoid with the cut halfway between the clamps. A continuous load was applied to the specimen such that the tear propagated across the specimen width. The force required to completely tear the specimen was recorded on a chart. The results were expressed in pounds or kilograms and higher numbers indicated a greater resistance to tearing and, therefore, a stronger material.

The surface smoothness of a material is another important feature of a material if the material is to be used as a body contacting layer as is the case with the present material when used as a liner for a sanitary napkin. The surface smoothness of the materials described herein was tested by measuring the coefficient of friction of the surface when contacted with a sensor plate drawn across the surface of the material. Values between materials were then compared to establish a relative scale for purposes of evaluation. Higher coefficients of friction corresponded to rougher surfaces.

A fluid run-off test was performed to measure the ability of a material to absorb a liquid. A 3 inch by 7 inch sample of the material was placed at a 30° incline and 5cc of synthetic menstrual fluid was then applied to the surface over a 3 second period. The amount of fluid which was not absorbed and therefore ran off the end of the sample was measured in grams. The lower the gram reading and thus the run-off, the higher was the degree of absorption of the material.

The absorption time test indicated the intake rate for a material using 8 cc of synthetic menstrual fluid. A 3 inch by 7 inch sample of the test material was insulted with 10cc of synthetic menstrual fluid delivered from a fluid reservoir having a 2 inch by 0.5 inch delivery slot. The time to absorb 8 cc of fluid was then measured in seconds. A lower absorption time as measured in seconds was an indication of a faster intake rate for the particular material.

Once a material has been insulted, it was also important to measure the amount of rewet that took place. Ten cubic centimeters of the synthetic menstrual fluid were delivered to the test specimen from a reservoir having a 2 inch by 0.5 inch delivery slot. Next a blotter was placed on top of the specimen and one pound per square inch of pressure was applied for a period of 3 minutes. After the 3 minute interval, the blotter paper was removed and weighed and the amount of menstrual fluid absorbed by the blotter paper was measured in grams. Higher values were an indication of a greater degree of rewet for the particular material tested.

The adhesion level between the film layer and the substrate layer is also important. To measure the adhesion level in kilograms per square inch between the two layers, an adhesion test was performed. For each sample, the cohesion force of a 1 inch square sample was measured using a Chatillon Digital Force Gauge Model DFI 50 from John Chatillon and Sons, Inc., of Greensboro, N.C. The device has a pneumatically operated base plate measuring 2 inches by 4 inches and a one inch square top plate which was connected to a digital force gauge. Double-faced adhesive tape was applied to both the base plate and the top plate and a 2 inch by 4 inch sample of material was positioned on top of the 2 inch by 4 inch base plate. The tape used to cover the surfaces of both the base plate and top plate was Scotch® Brand double-coated pressure-sensitive tape number 406, which is available in 1-inch and 2-inch widths. The 2-inch width tape was used for the base plate and the 1-inch wide strip tape was used for the top plate. Once the sample had been placed on top of the base plate, the base plate and sample were compressed for a period of 3 seconds under a pressure of 60 pounds per square inch. After 3 seconds, the pressure was released. The digital force gauge was then activated and the sample was compressed between the base plate and top plate at 60 psi for a period of 10 seconds. Next, the base plate was drawn away from the top plate and the separation force was measured in kilograms per square centimeter. The amount of force required to separate the laminate was then recorded.

To measure the Starrett Bulk or bulk of the material which relates to the thickness of the material, five inch by five inch (127 millimeter×127 millimeter) samples of material were compressed under a load of 0.05 pounds per square inch and the thickness of the material was measured while the sample was under compression. Higher numbers indicated thicker, more bulky materials.

EXAMPLE I

In Example I a series of 24 samples were prepared to demonstrate the present invention and its properties. The film and nonwoven substrate layers were the same for each sample with the basis weight and fiber size of the nonwoven web being the variable. With all examples the film layer was a 1 mil polyethylene film made by Edison Plastics Company of Plainfield, N.J. containing approximately 4% by weight titanium dioxide opacifying agent based upon the total weight of the film. The film was slit using a pair of matched male/female steel perforating/embossing rolls. Pair of slits were cut into the film in the pattern shown in FIG. 1. Each slit was 0,165 inches (4.2 mm) in length. The spacing between slits in a pair was 0.035 inches (0.9 mm) and the spacing between each pair of slits lying along the same horizontal line or row was 0,145 inches (3.7 mm). Vertically, between adjacent pairs of slits in a column, the pairs of slits were spaced 0.015 inches (0.4 mm) apart. As will be readily appreciated, the film can be slit in line or ahead of time and then unrolled into the converting process. The film had a slit density of 19 inches of slits per square inch (7.48 cm/cm$^2$) of film.

The substrate layer in Example I was a fibrous bicomponent spunbond web made in the manner described above. Fiber sizes ranged between 3 and 5 denier (21.9 and 28.2 microns) and the fibers due to the use of the spunbond process were essentially continuous in length. By "continuous" it is meant that the ratio of fiber length to width approached infinity. The bicomponent fibers were a side-by-side construction using polyethylene and polypropylene. The polyethylene was Grade 6811 from Dow Chemical, U.S.A. of Midland, Mich. and the polypropylene was Grade 3445 from Exxon Chemical Company of Darien, Conn. Basis weights ranged between 1 and 1.5 ounces per square yard (osy) (34–51 gsm) and the webs were through air bonded.

The nonwoven substrate layer was treated with Y12488 surfactant from Union Carbide of Tarrytown, N.Y. This is a non-ionic surfactant wetting packaging which references U.S. Pat. No. 5,057,361. The surfactant was added in spray form and the treated nonwoven web had an add on of 0.4 percent surfactant based upon the total dry weight of the nonwoven web.

Prior to bonding the two layers together, the nonwoven layer was stretched between 5 and 20 percent due to the speed differential of the rolls. See the process description above. As an example, a material that was originally 100 inches (254 cm) in length and which was then stretched to 120 inches (305 cm) would be stretched 20 percent.

$$\frac{\text{stretched length} - \text{original length}}{\text{original length}} \times 100 = \% \text{ stretch}$$

$$\frac{120 - 100}{100} \times 100 = 20\%$$

The film and substrate layers were point bonded to one another using conventional ultrasonic equipment from Branson Sonic Power Corp of Danbury, Conn. using a model #501 series bonder. The relative energy was 65 and the line speed at the point of bonding was 12 feet per minute (3.7 meters per minute). Total bond area per unit area of material was eight percent with approximately 28 bond points per square inch (4.34 points/cm$^2$). The gap setting between the horn and anvil was 0.010 inches (0.3 mm).

Once the film and nonwoven layers were bonded to one another, the nonwoven substrate layer was allowed to relax thereby causing the composite to gather or pucker which in turn caused a plurality of the slits to vertically open up and form paths for greater transmission of liquids through the composite. After the composite was formed it was then hand sprayed on the exposed film surface with the same surfactant used on the nonwoven layer at an add on level of 0.4 percent on a dry weight basis, based upon the total weight of the film. The compositions of the samples are listed in Table I below.

TABLE I

| SAMPLE # | FILM THICKNESS (mils) | NONWOVEN FIBER SIZE (microns) | BASIS WT. (gsm) | STRETCH (%) |
|---|---|---|---|---|
| 1 | 1 | 21.9 | 34 | 5 |
| 2 | 1 | 21.9 | 34 | 10 |
| 3 | 1 | 21.9 | 34 | 15 |
| 4 | 1 | 21.9 | 34 | 20 |
| 5 | 1 | 21.9 | 51 | 5 |
| 6 | 1 | 21.9 | 51 | 10 |
| 7 | 1 | 21.9 | 51 | 15 |
| 8 | 1 | 21.9 | 51 | 20 |
| 9 | 1 | 25.1 | 34 | 5 |
| 10 | 1 | 25.1 | 34 | 10 |
| 11 | 1 | 25.1 | 34 | 15 |
| 12 | 1 | 25.1 | 34 | 20 |

TABLE I-continued

| SAMPLE # | FILM THICKNESS (mils) | NONWOVEN FIBER SIZE (microns) | BASIS WT. (gsm) | STRETCH (%) |
|---|---|---|---|---|
| 13 | 1 | 25.1 | 51 | 5 |
| 14 | 1 | 25.1 | 51 | 10 |
| 15 | 1 | 25.1 | 51 | 15 |
| 16 | 1 | 25.1 | 51 | 20 |
| 17 | 1 | 28.2 | 34 | 5 |
| 18 | 1 | 28.2 | 34 | 10 |
| 19 | 1 | 28.2 | 34 | 15 |
| 20 | 1 | 28.2 | 34 | 20 |
| 21 | 1 | 28.2 | 51 | 5 |
| 22 | 1 | 28.2 | 51 | 10 |
| 23 | 1 | 28.2 | 51 | 15 |
| 24 | 1 | 28.2 | 51 | 20 |

Once the composite samples were formed, a series of tests were performed including MD and CD trap tear, Frazier porosity, Starret bulk and adhesion or peel strength between surfaces. These properties are presented in Table II below.

TABLE II

| SAMPLE # | BULK (mm) | MD TRAP TEAR (Kg) | CD TRAP TEAR (Kg) | POROSITY (scfm) | ADHESION (kg/cm$^2$) |
|---|---|---|---|---|---|
| 1 | 0.040 | 2.71 | 0.9 | 100 | 0.37 |
| 2 | 0.046 | 2.8 | 1.0 | 129 | 0.33 |
| 3 | 0.048 | 2.9 | 0.9 | 143 | 0.39 |
| 4 | 0.054 | 2.9 | 1.0 | 168 | 0.38 |
| 5 | 0.057 | 3.4 | 1.5 | 116 | 0.44 |
| 6 | 0.061 | 3.5 | 1.7 | 134 | 0.40 |
| 7 | 0.063 | 3.7 | 1.6 | 152 | 0.41 |
| 8 | 0.069 | 3.9 | 1.6 | 168 | 0.41 |
| 9 | 0.044 | 2.0 | 0.9 | 71 | 0.30 |
| 10 | 0.041 | 1.9 | 0.8 | 86 | 0.35 |
| 11 | 0.044 | 1.9 | 0.8 | 112 | 0.39 |
| 12 | 0.049 | 2.2 | 0.7 | 155 | 0.37 |
| 13 | 0.057 | 2.7 | 1.1 | 127 | 0.35 |
| 14 | 0.060 | 3.0 | 1.2 | 143 | 0.36 |
| 15 | 0.064 | 3.1 | 1.1 | 162 | 0.35 |
| 16 | 0.064 | 3.2 | 0.9 | 175 | 0.35 |
| 17 | 0.046 | 1.8 | 0.6 | 98 | 0.31 |
| 18 | 0.047 | 2.1 | 0.5 | 132 | 0.26 |
| 19 | 0.048 | 1.9 | 0.5 | 136 | 0.34 |
| 20 | 0.053 | 2.0 | 0.4 | 157 | 0.32 |
| 21 | 0.055 | 2.6 | 0.8 | 105 | 0.31 |
| 22 | 0.061 | 2.6 | 0.9 | 128 | 0.33 |
| 23 | 0.062 | 2.4 | 0.9 | 140 | 0.32 |
| 24 | 0.061 | 2.5 | 0.9 | 158 | 0.33 |

As can be seen from Tables I and II, as the percent stretch was increased, the bulk and porosity were increased. All the sample materials had acceptable tear strengths and adhesion values. The degree of openness of the overall composite is a function of, at least in part, the degree of puckering which in turn governs how little or how much the slits in the film layer 12 open to permit passage of fluids.

In addition to testing of the composite samples by themselves, swatches of each of the twenty-four samples were cut and placed on top of a two layer absorbent core with the nonwoven side adjacent the absorbent to simulate the cover material of a personal care absorbent article, in this case a feminine pad or sanitary napkin. The top, body side layer of the core was a 425 gsm fluff with a density of 0.07 g/cc and the baffle-side layer was a 470 gsm fluff with a density of 0.094 g/cc. The baffle-side layer was embossed.

One method of measuring the openness and thus the fluid handling properties of the composite 10 is by measuring the intake time for a given quantity of fluid. The samples were tested for fluid intake time (8 cc), rewet (10 cc) and fluid run off (5 cc) using "Z-Date" a synthetic menstrual fluid containing, on a weight percent basis, approximately 82.5% water, 15.8% polyvinyl pyrrolidone and 1.7% salts, coloring agents and surfactants. It has a viscosity of 17 centipoise and a surface tension of 53.5 dynes per centimeter. The results are given in Table III below. As shown by the data in Table III below, intake rates for "Z-DATE" synthetic menstrual fluid were on the average less than 10 seconds. Once the synthetic menses had been absorbed, the rewet was less than 0.5 grams.

TABLE III

| SAMPLE # | 8 cc INTAKE (sec) | 10 cc REWET (grams) | 5 cc RUN-OFF (grams) |
| --- | --- | --- | --- |
| 1 | 10.14 | 0.26 | 1.4 |
| 2 | 7.45 | 0.25 | 0.4 |
| 3 | 6.86 | 0.18 | 0.2 |
| 4 | 5.68 | 0.18 | 0 |
| 5 | 9.14 | 0.11 | 1.2 |
| 6 | 6.92 | 0.13 | 0.7 |
| 7 | 5.97 | 0.08 | 0.1 |
| 8 | 5.32 | 0.06 | 0 |
| 9 | 11.56 | 0.37 | 1.6 |
| 10 | 10.33 | 0.44 | 1.5 |
| 11 | 7.82 | 0.29 | 0.7 |
| 12 | 5.67 | 0.14 | 0 |
| 13 | 7.97 | 0.12 | 0.6 |
| 14 | 7.52 | 0.13 | 0.3 |
| 15 | 6.40 | 0.13 | 0.1 |
| 16 | 5.58 | 0.08 | 0 |
| 17 | 10.03 | 0.39 | 0.9 |
| 18 | 7.53 | 0.28 | 0.3 |
| 19 | 7.04 | 0.19 | 0.2 |
| 20 | 6.53 | 0.11 | 0 |
| 21 | 9.34 | 0.36 | 0.7 |
| 22 | 7.33 | 0.23 | 0.1 |
| 23 | 6.99 | 0.19 | 0.1 |
| 24 | 6.17 | 0.10 | 0.1 |

Overall the material of the present invention performed very well as a cover material for the body side of a feminine pad with the film positioned adjacent the wearer. The film layer was soft to the touch and the composite provided excellent intake of the synthetic menses and minimal rewet. Generally for 10 grams of Z-date added, less than 5 percent of the initial insult rewetted the surface. In addition because the intake rate was so good, very little liquid ran off the pad.

It is believed that this excellent performance was due to the openness of the slits in the "Z" direction and the undulating, three-dimensional surface with the slits residing in a multiplicity of planes to provide good fluid flow into the nonwoven layer below. In addition, because the openings in the film layer were primarily in the "Z" direction as opposed to the X-Y plane of the film, stain masking was also good. The lofty, low density nonwoven layer below the film surface provided temporary storage of the fluid while it was being desorbed into the absorbent core. Furthermore, the nonwoven layer acted as a means for separating the user from the absorbent core.

Caliper or bulk is a measure of the thickness of a material. While again depending upon the particular end use application, for personal care applications calipers of at least about 0.035 inches (0.15 mm) are desirable so as to prevent rewet of the film layer 12 by already absorbed exudate contained within the absorbent core of the personal care structure.

For personal care product applications, the composite should have sufficient strength and integrity against delamination so as to not delaminate or otherwise break down during use. As a result, delamination values should be in excess of 0.16 kg/cm$^2$. Typically in such applications the composite will have a trapezoidal tear strength of at least about 0.5 lbs. (0.23 kg) in both the machine and cross-directions relative to the machine and cross-direction of the nonwoven substrate layer.

EXAMPLE II

In Example 2, four sample materials according to the present invention were prepared and compared against two controls. The first control was a KOTEX® Maxi Pad sanitary napkin manufactured by the assignee of record. The napkin had a polypropylene spunbond nonwoven cover. The second control was an ALWAYS® sanitary napkin manufactured by the Procter and Gamble Company of Cincinnati, Ohio. The ALWAYS® sanitary napkin had an apertured film cover.

The film layer for all four samples of the present invention was the same as that used in Example 1. The substrate layer was the same type as that used in Example 1, a fibrous spunbond bicomponent nonwoven web using 3 denier polyethylene/polypropylene side-by-side bicomponent fibers. The basis weight of the fibrous nonwoven web was 0.8 ounces per square yard (27 gsm) and the web was through-air bonded.

Prior to the bonding of the film and fibrous nonwoven layers, the nonwoven layer was stretched in the machine direction to elongate it. The degree of neck stretch as shown in Table IV below was calculated using the formula below:

$$\frac{\text{Original width} - \text{Final width}}{\text{Original width}} \times 100 = \% \text{ neck stretch}$$

As can be seen from Table IV below, sample 1 had no stretching of the nonwoven layer. Samples 2, 3 and 4 were made using increased degrees of stretch as represented by the values of 17, 27 and 40%.

The film and substrate layers were bonded to one another using heat and pressure via a pair of patterned and anvil bond rolls. The patterned roll was heated to 140° F. (60° C.) and the anvil roll was heated to 160° F. (71° C.). The bond pressure at the nip was 20 pounds per square inch (6.8 kg/cm$^2$) and the two layers were bonded to one another at a rate of 10 feet per minute (3m/min) using a point bond pattern with an overall bond area of 8%. Once the composites were made, the exposed sides of the nonwoven and film layers were hand sprayed with a surfactant solution of Gemtex SM-33 surfactant from Finetex, Inc. of Elmwood Park, N.J. at an add-on of 0.6% based on the weight of the composite.

Once the samples were prepared, they were placed on the KOTEX® Maxi Pad chassis and compared to the two controls. The Kotex® Maxi Pad had a plastic film as the outer cover or baffle material and a 0.4 osy polypropylene spunbond fibrous nonwoven liner which was removed and replaced with samples of the present invention. The portion of the absorbent core closest to the liner comprised six plies of creped tissue body wadding each of which weighed 19 gsm. Below this layer there was a single layer of 19 gsm tissue which surrounded a 6.86 gram fluff batt having a density of 0.07 grams/cc. For samples 1 through 4, the coverstock from the KOTEX® Maxi Pad feminine pad was removed and pieces of the sample materials were laid on top of the pad with no gluing. The fibrous nonwoven layer was positioned adjacent the absorbent core. The samples of the present invention and the controls were then tested for bulk, intake rate, rewet and run-off. The results are shown in Table IV below.

TABLE IV

| SAM-PLE | LINER | % Stretch | BULK (mm) | IN-TAKE RATE (sec) | REWET (g) | RUN-OFF (g) |
| --- | --- | --- | --- | --- | --- | --- |
| 1 | Film/NW | 0 | 1.4 | 13.0 | 0.07 | 0.6 |
| 2 | Film/NW | 17 | 1.7 | 7.7 | 0.06 | 0.0 |
| 3 | Film/NW | 27 | 2.2 | 6.4 | 0.06 | 0.0 |
| 4 | Film/NW | 40 | 2.3 | 5.2 | 0.04 | 0.0 |
| CONTROL | KOTEX® pad | — | 0.25 | 16.0 | 1.20 | 3.9 |
| CONTROL | ALWAYS® pad | — | 0.25 | 9.0 | 0.30 | 0.4 |

As can be seen from Table IV, the bulk increased with the increase in the percentage of stretching of the fibrous nonwoven web substrate layer. As the percent of stretching of the nonwoven layer was increased prior to bonding of the two layers, the resultant puckering of the surface of the composite and in particular the film layer was also increased. As a result, there was a dramatic decrease in the amount of time needed to pass 8 cc of the synthetic menstrual fluid through the coverstock. The KOTEX® Maxi Pad sanitary napkin control took 16 seconds to absorb the 8 cc of fluid. The ALWAYS® pad control took 9 seconds to absorb 8 cc of fluid. The nonstretched film nonwoven laminate took 13 seconds but once stretch was imparted to the material as was the case in samples 2, 3 and 4, the intake time dramatically decreased to a low value of 5.2 seconds which was a third of the time needed to absorb the same amount of liquid with respect to the KOTEX® Maxi Pad control.

The amount of rewet was also dramatically decreased with the material of the present invention. The KOTEX® Maxi Pad control exhibited a 1.20 gram rewet and the ALWAYS® pad exhibited a 0.3 gram rewet whereas the samples of the present invention had values less than one tenth of a gram. Thus, it can been seen that the quilted film laminate of the present invention can be used as a coverstock which dramatically increases intake time and reduces the amount of fluid that ultimately rewets the surface.

A 5 cc run-off test was also performed in accordance with the test procedures described above. Relative to the KOTEX® Maxi Pad control, it can be seen that there was a dramatic decrease in the amount of fluid which ran off the surface of the pad due to the three-dimensional surface which translates into a coverstock which should result in lower leakage for the user.

EXAMPLE III

In Example 3, three samples according to the present invention were prepared all of which used the same substrate layer. The substrate layer was made in the same fashion as Examples 1 and 2 using 5 denier polyethylene/polypropylene side-by-side bicomponent fibers. The substrate layer had a basis weight of 1.5 ounces per square yard (51 gsm) and was treated with 0.4% of the same surfactant used in Example 1.

The variable in Example 3 was the film layer. For sample 1, the film layer was a 1 mil thick polyethylene film containing 4% by weight titanium dioxide made by Edison Plastics of Plainfield, N.J. Sample 2 was a 1 mil thick low density polyethylene film made from, on a total weight percent basis, 76% NA206 low density polyethylene from Quantum, Inc. of Wallingford, Conn. and 24% 41171 pigment which contains 12% by weight titanium dioxide from Ampacet Company of Mount Vernon, N.Y. Sample 3 was a 1 mil elastomeric copolymer film made from 76% by weight Himont KS072 resin and 24% by weight of the 41171 pigment. The Himont KS072 resin is available from Himont, Inc. U.S.A. of Wilmington, Del. Each of these films was slit in the same manner as the film used in Example 1. Prior to bonding, the substrate layer for each of the samples was stretched and then bonded to the film layer with the percent stretch equaling 20% for all three samples. The composites once formed were hand sprayed with 0.4% by weight of the Union Carbide Y12488 surfactant on the exposed film side of each of the samples. The controls for Example 3 were the same as described in Example II. For samples 1 through 3, the coverstock of a KOTEX® Maxi Pad was removed and replaced with pieces of the three samples in the same fashion as with the previous examples. All three samples plus the two controls were then measured for bulk, porosity, adhesion between layers, CD trapezoidal tear, intake rate, rewet, run-off values and surface smoothness. The results of these tests are shown in Table V below.

TABLE V

| SAMPLE | BULK (mm) | POROSITY (scfm) | ADHESION (kg/cm$^2$) | CD TEAR (kg) | 8 cc Intake (sec) | 10 cc Rewet (g) | 5 cc Run-off (g) |
| --- | --- | --- | --- | --- | --- | --- | --- |
| 1 | 1.5 | 158 | 0.33 | 0.9 | 6.2 | 0.10 | 0.1 |
| 2 | 1.4 | 139 | 0.33 | 0.8 | 7.5 | 0.16 | 0.3 |
| 3 | 1.5 | 155 | 0.06 | 0.8 | 8.2 | 0.21 | 0.2 |
| KOTEX® CONTROL | 0.25 | — | — | 1.2 | 16.0 | 1.2 | 3.9 |
| ALWAYS® CONTROL | 0.25 | 792 | — | 1.0 | 9.0 | 0.30 | 0.4 |

Adhesion values were not obtained for the controls as they were single layer cover materials. As can be seen from the data in Table V, the three samples according to the present invention were all bulkier than either of the controls. Their CD trapezoidal tears, intake rates, rewet and run-off values all surpassed both of the controls. Adhesion levels for samples 1 and 2 were good but sample 3 in this particular case tore too easily. The surface smoothness for the film surfaces of the composites were all acceptable. Each of the composites was soft to the touch and had a cloth-like feel. Based upon Example III it should be noted that the smoothness and cloth-like feel of the laminate can be altered based upon the film polymer selection. Sample 3 (elastomeric copolymer film) was smoother than Sample 2 (LDPE film) which in turn was smoother than Sample 1 (PE film).

EXAMPLE IV

In Example 4, the film and substrate layers used were the same as in Example 2. The difference between Example 4 and Example 2 was in the slit pattern used to slit the film layer. In Example 4, a herringbone design similar to that shown in FIG. 2 was used. The herringbone design yielded an average slit length per square inch of 16.3 in/in$^2$ (6.4 cm/cm$^2$). In addition, as opposed to using heat and pressure to bond the film and substrate layers together, in Example 4, 10 grams per square meter of a 34-5541 hot-melt adhesive from the National Starch Company of Cincinnati, Ohio was applied in continuous spray pattern across the width of the nonwoven layer. Prior to bonding the two layers together, the film layer was stretched in the machine direction and the percent stretch was calculated to be 5%. After forming the sample, it was hand-sprayed with 0.6%, based upon the dry weight of the composite, with Gemtex SM-33 surfactant on the exposed sides of the film and substrate layers. Fluid handling properties including bulk, intake and rewet rates were measured and are given below in Table VI below. Relative to the two controls, the sample in Example IV had a much better intake rate and far less rewet. In addition, there was no run-off of synthetic menses with the herringbone slit design. Lastly, it should be noted that the same good fluid handling properties were achieved using an adhesively laminated composite instead of a thermally laminated composite.

TABLE VI

| SAMPLE | BULK (mm) | 8 cc INTAKE (sec) | 10 cc REWET (g) | 5 cc RUN-OFF (g) |
| --- | --- | --- | --- | --- |
| 1 | 1.8 | 6.3 | 0.12 | 0 |
| KOTEX ® CONTROL | 0.25 | 16.0 | 1.20 | 3.9 |
| ALWAYS ® CONTROL | 0.25 | 9.0 | 0.30 | 0.4 |

Having thus described the invention in detail it should be appreciated that various modifications and changes can be made in the present invention without departing from the spirit and scope of the following claims.

We claim:

1. A process for forming a quilted film laminate comprising:

placing a film layer defining a plurality of generally parallel slits in generally face-to-face relationship with a substrate layer, bonding said film layer to said substrate layer to form a composite, causing at least one of said film layer and said substrate layer to retract to form a plurality of puckers in said film layer with a plurality of said slits defining openings which reside in, above and below a central plane defined by said film layer.

2. The process of claim 1 wherein said substrate layer is heat-shrinkable and said composite is heated to retract said heat-shrinkable substrate layer and form said plurality of puckers.

3. The process of claim 2 wherein said film layer is stretched prior to the bonding of said film layer to said heat-shrinkable substrate layer.

4. A process for forming a quilted film laminate comprising:

stretching a substrate layer, bonding a film layer defining a plurality of generally parallel slits therein to said substrate layer to form a composite, retracting said substrate layer to form a plurality of puckers in said film layer and a plurality of said slits to define openings in said film layer with said slits residing in, above and below a central plane defined by said film layer.

5. The process of claim 4 wherein said substrate layer is stretched in at least two directions before being bonded to said film layer.

6. The process of claim 4 wherein said film layer is stretched in a first direction and said substrate layer is stretched in a second direction before said bonding step.

7. The process of claim 4 wherein said film layer is stretched prior to bonding said film layer to said substrate layer.

8. A quilted film laminate comprising:

a film layer defining a plurality of generally parallel slits, said film layer further defining a central plane, a substrate layer bonded to said film layer to form a composite, said composite having a plurality of puckers, said slits defining a plurality of openings in said film layer which reside in, above and below said central plane.

9. The quilted film laminate of claim 8, said substrate layer is bonded to said film layer at a plurality of spaced apart bond sites.

10. The quilted film laminate of claim 8 wherein said substrate layer is a fibrous nonwoven web.

11. The quilted film laminate of claim 10 wherein said film layer contains an opacifying agent.

12. The quilted film laminate of claim 11 wherein said opacifying agent is titanium dioxide and is present in said film layer in a weight percent of from about 4 to about 12 percent based upon the total weight of said film layer.

13. The quilted film laminate of claim 8 wherein each of said slits in said film layer define a slit length and wherein said film layer defines a total slit length per square inch of said film layer of at least 5 inches per square inch.

14. The quilted film laminate of claim 10 wherein said fibrous nonwoven web includes a plurality of bicomponent fibers.

15. A personal care absorbent article comprising a body side liner and a back side liner with an absorbent core disposed therebetween, said body side liner comprising the quilted film laminate of claim 8.

16. The personal care absorbent article of claim 15 wherein said personal care absorbent article is a feminine napkin.

17. The personal care absorbent article of claim 15 wherein said personal care absorbent article is a diaper.

18. The personal care absorbent article of claim 15 wherein said personal care absorbent article is a training pant.

19. The personal care absorbent article of claim 15 wherein said personal care absorbent article is an incontinence garment.

20. The personal care absorbent article of claim 15 wherein said personal care absorbent article is a bandage.

21. A surgical drape wherein at least a portion of said surgical drape comprises the quilted film laminate of claim 8.

* * * * *

UNITED STATES PATENT AND TRADEMARK OFFICE
CERTIFICATION OF CORRECTION

PATENT NO. : 5,536,555

DATED : July 16, 1996

INVENTOR(S): Zelazoski et al

It is certified that the following errors appear in the above-identified patent and that said Letters Patent is hereby corrected as shown below:

Column 5, line 19, "18b." should read --18b'.--;

Column 12, line 54, "0,165" should read --0.165--;

Column 12, line 57, "0,145" should read --0.145--;

Signed and Sealed this

Seventeenth Day of December, 1996

Attest:

BRUCE LEHMAN

*Attesting Officer*     *Commissioner of Patents and Trademarks*